(12) United States Patent
Lee et al.

(10) Patent No.: US 8,455,045 B2
(45) Date of Patent: Jun. 4, 2013

(54) HIGH SENSITIVE GAS SENSOR USING CARBON MATERIALS CONTAINING IONIC METAL CATALYST AND MANUFACTURING METHOD THEREOF

(75) Inventors: Young Seak Lee, Daejeon (KR); Seok Chang Kang, Daejeon (KR); Sung Kyu Lee, Daejeon (KR); Ji Sun Im, Daejeon (KR)

(73) Assignee: Chungnam National Industry Collaboration Foundation, Daejeon (KR)

( * ) Notice: Subject to any disclaimer, the term of this patent is extended or adjusted under 35 U.S.C. 154(b) by 394 days.

(21) Appl. No.: 12/974,784

(22) Filed: Dec. 21, 2010

(65) Prior Publication Data

US 2012/0045574 A1    Feb. 23, 2012

(30) Foreign Application Priority Data

Aug. 23, 2010   (KR) ........................ 10-2010-0081674

(51) Int. Cl.
*B05D 5/12* (2006.01)
(52) U.S. Cl.
USPC ....... 427/126.4; 427/126.3; 427/58; 204/427; 204/431

(58) Field of Classification Search
USPC ............ 427/58, 112, 113, 122, 126.3, 126.4; 204/424, 431; 977/953
See application file for complete search history.

(56) References Cited

U.S. PATENT DOCUMENTS

| 7,378,008 B2 * | 5/2008 | Inoue et al. .................. 204/430 |
| 2011/0143023 A1 * | 6/2011 | Lee et al. .................. 427/126.3 |

* cited by examiner

*Primary Examiner* — Michael Cleveland
*Assistant Examiner* — Tabassom Tadayyon Eslami
(74) *Attorney, Agent, or Firm* — Kile Park Reed & Houtteman PLLC

(57) ABSTRACT

Disclosed is a high sensitive gas sensor using a carbon material containing an ionized metal catalyst and a method of manufacturing the same. The method includes the steps of: (1) preparing a hydroxide solution by dissolving a hydroxide in a distilled water; (2) dissolving a metal catalyst in the hydroxide solution; (3) immersing the carbon material in a solution obtained through step (2) and stirring the carbon material; (4) heat-treating a mixture obtained through step (3); (5) cleaning the heat-treated carbon material obtained through step (4); (6) drying the carbon material cleaned through step (5); and (7) manufacturing the gas sensor by loading the carbon material obtained through step (6) on a substrate. The gas sensor having high sensitivity and responsiveness with respect to a target gas even in a normal temperature is obtained.

18 Claims, 3 Drawing Sheets

HIGH SENSITIVE GAS SENSOR USING CARBON MATERIALS CONTAINING IONIC METAL CATALYST AND MANUFACTURING METHOD THEREOF

BACKGROUND OF THE INVENTION

1. Field of the Invention

The present invention relates to a high sensitive gas sensor using carbon materials containing an ionic metal catalyst and a manufacturing method thereof. More particularly, the present invention relates to a method of manufacturing a high sensitive gas sensor, in which a metal catalyst is ionized and the ionized metal catalyst is evenly introduced into a carbon material to form a fine structure in the carbon material, so that the high sensitive gas sensor can be manufactured by using the carbon material.

2. Description of the Related Art

In general, $NO_R$, $CO_x$ and $SO_x$ gases, which are generated during the combustion process in the power plant, the waste incinerator and the combustion engine of the vehicle, may cause photochemical smog and acid rain. These gases are very harmful to the human body, but may not be sensed by the sensory organ of the human body, so a sensor capable of sending these gases in the early stage must be developed. A metal oxide semiconductor, such as $SnO_2$, a solid electrolytic material, various organic substances, and a complex of a carbon black and an organic substance have been used for the materials of the gas sensor. However, the gas sensor manufactured by using the above materials represents many problems, such as limitation of application fields. In the case of the gas sensor manufactured by using the metal oxide semiconductor or the solid electrolytic material, the gas sensor can be normally operated when the high temperature of 200° C. to 600° C. or above is applied to the gas sensor. In the case of the gas sensor manufactured by using the organic substance, the electric conductivity is very low. In addition, in the case of the gas sensor manufactured by using the complex of the carbon black and the organic substance, the sensitivity is very low. Further, the gas sensor manufactured by using the above material represents the low sensitive time and the low recovery rate. In addition, the gas sensor is very expensive, so that the gas sensor is not extensively used.

SUMMARY OF THE INVENTION

The present invention has been made to solve the problems occurring in the related art, and an object of the present invention is to provide a gas sensor having high sensitivity and responsiveness with respect to target gas even in the normal temperature and a method of manufacturing the same, in which a metal catalyst is ionized and the ionized metal catalyst is evenly introduced into a carbon material to form a fine structure in the carbon material, so that the high sensitive gas sensor can be manufactured by using the carbon material.

In order to accomplish the above object, according to one embodiment of the present invention, there is provided a method of manufacturing a high sensitive gas sensor using a carbon material containing an ionized metal catalyst. The method includes the steps of (1) preparing a hydroxide solution by dissolving a hydroxide in a distilled water; (2) dissolving a metal catalyst in the hydroxide solution; (3) immersing the carbon material in a solution obtained through step (2) and stirring the carbon material; (4) heat-treating a mixture obtained through step (3); (5) cleaning the heat-treated carbon material obtained through step (4); (6) drying the carbon material cleaned through step (5); and (7) manufacturing the gas sensor by loading the carbon material obtained through step (6) on a substrate.

According to the exemplary embodiment of the present invention, the hydroxide includes one selected from the group consisting of a potassium hydroxide, a sodiumhydroxide, a lithium hydroxide, a rubidium hydroxide, a cesium hydroxide and a mixture thereof. A density of the hydroxide solution prepared through step (1) is in a range of 2M to 8M, preferably, in a range of 4M to 6M.

According to the exemplary embodiment of the present invention, the metal catalyst dissolved in the hydroxide solution in step (2) includes a metal oxide catalyst including oxygen. In detail, the metal oxide catalyst includes one selected from the group consisting of $ZnO_2$, $CuO_2$, $V_2O_5$, $Fe_2O_3$, $MnO_2$, $MgO_2$, $CrO_2$, $AlO_2$, and a mixture thereof.

According to the exemplary embodiment of the present invention, 5 to 40 weight part of the metal catalyst is dissolved in 100 weight part of the hydroxide solution in step (2).

According to the exemplary embodiment of the present invention, various types of carbon materials generally known in the art can be used. For instance, the carbon material includes one selected from the group consisting of a single-wall carbon nano tube, a dual-wall carbon nano tube, a multi-wall carbon nano tube, a carbon fiber, a carbon black, a graphite, a char, a coal, a tar and a mixture thereof.

According to the exemplary embodiment of the present invention, the carbon material is immersed and stirred for 0.5 to 3 hours under a normal temperature in step (3).

According to the exemplary embodiment of the present invention, in step (3), 5 to 20 weight part of the carbon material is immersed and stirred in 100 weight part of the solution obtained through step (2).

According to the exemplary embodiment of the present invention, in step (4), the heat-treating for the mixture is performed for 1 to 4 hours under a temperature range of 600° C. to 900° C. by rising a temperature at a rate of 5° C. to 10° C./min.

According to the exemplary embodiment of the present invention, in step (5), the carbon material is repeatedly cleaned by using the distilled water until a cleaning liquid has a neutral PH after the cleaning.

According to the exemplary embodiment of the present invention, in step (6), the carbon material is dried for 5 to 30 hours under a temperature range of 50° C. to 100° C.

According to the exemplary embodiment of the present invention, in step (7), the gas sensor is manufactured by dispersing the carbon material obtained through step (6) in a dispersing solution and depositing the dispersing solution on the substrate formed thereon with an electrode.

According to the exemplary embodiment of the present invention, the dispersing solution includes one selected from the group consisting of ethanol, methanol, acetone, dimethylformamid, and a mixture thereof. The amount of the carbon material contained in the dispersing solution is 0.1 to 10 weight part based on 100 weight part of the dispersing solution.

According to the exemplary embodiment of the present invention, the method further includes a step of heat-treating the gas sensor obtained through step (7).

According to another aspect of the present invention, there is provided a high sensitive gas sensor using a carbon material containing an ionic metal catalyst manufactured according to the above method.

As described above, according to the present invention, the metal catalyst is ionized and the ionized metal catalyst is evenly introduced into the carbon material to form the fine structure in the carbon material through the activation process, and the gas sensor is manufactured by using the carbon material, so that the gas sensor having high sensitivity and responsiveness with respect to target gas even in the normal temperature can be achieved.

DETAILED DESCRIPTION OF THE INVENTION

Figure 1:
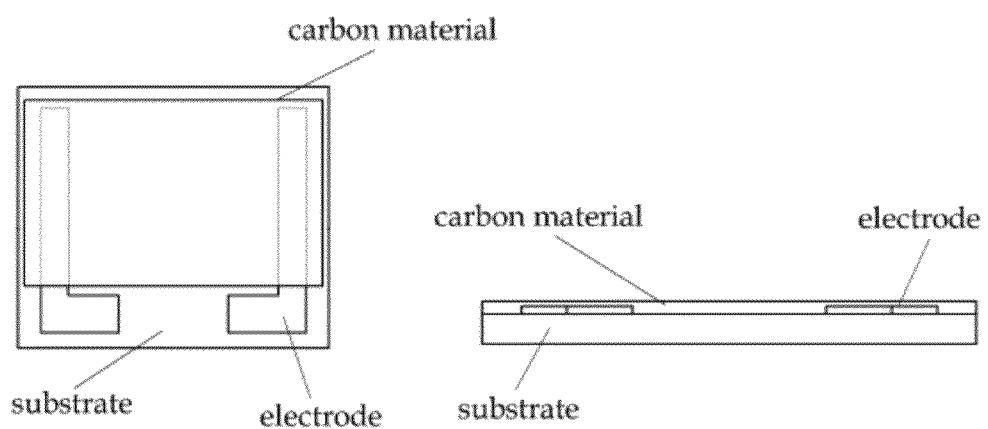
FIG. 1 is a schematic view showing a gas sensor manufactured according to the embodiment of the present invention.
Figure 2:
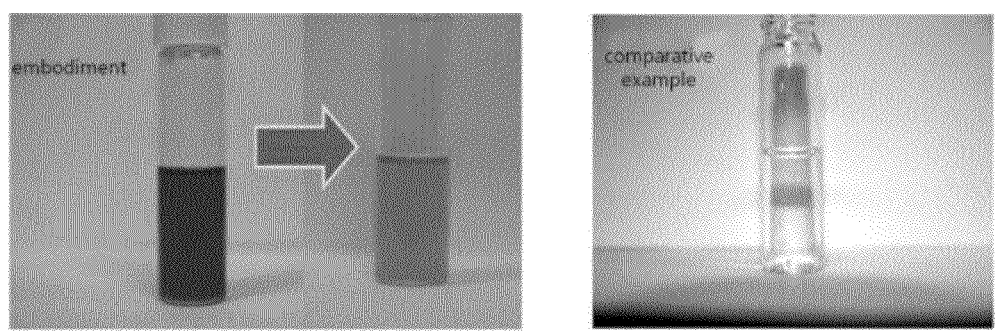
FIG. 2 is a photographic view showing a hydroxide solution containing ionized metal catalysts manufactured according to the embodiment of the present invention and the comparative example.

Hereinafter, the exemplary embodiments of the present invention will be described in detail with reference to accompanying drawings.

The present invention provides a method of manufacturing a high sensitive gas sensor using a carbon material containing an ionized metal catalyst. According to one embodiment of the present invention, the method includes the steps of (1) preparing a hydroxide solution by dissolving a hydroxide in a distilled water; (2) dissolving a metal catalyst in the hydroxide solution; (3) immersing the carbon material in a solution obtained through step (2) and stirring the carbon material; (4) heat-treating a mixture obtained through step (3); (5) cleaning the heat-treated carbon material obtained through step (4); (6) drying the carbon material cleaned through step (5); and (7) manufacturing the gas sensor by loading the carbon material obtained through step (6) on a substrate.

According to the present invention, the metal catalyst is ionized and the ionized metal catalyst is introduced into the carbon material to form the fine structure in the carbon material through the activation process. Then, the gas sensor is manufactured by using the carbon material. In order to form the fine structure in the carbon material through the dissolution and activation of the metal catalyst, the present invention uses strongly basic solution. Thus, the hydroxide solution used in step (1) is preferably a strongly basic hydroxide solution selected from the group consisting of a potassium hydroxide, a sodium hydroxide, a lithium hydroxide, a rubidium hydroxide, a cesium hydroxide and a mixture thereof.

In addition, a density of the hydroxide solution prepared through step (1) is preferably in the range of 2M to 8M, more preferably, in the range of 4M to 6M. If the density of the hydroxide solution is less than the lower limit level, it is difficult to dissolve the metal catalyst and to form the fine structure in the carbon material. If the density of the hydroxide solution exceeds the upper limit level, it is difficult to manufacture the gas sensor in the normal temperature, and the explosion may occur due to the strong exothermic reaction. In addition, the conductive band of the carbon material may be damaged due to the strong activation reaction, so that the sensitivity of the gas sensor may be degraded. If the density of the hydroxide solution is in the range of 4 to 8M, the hydroxide solution can be easily controlled and the optimal effect can be realized.

The metal catalyst dissolved in the hydroxide solution in step (2) may include various catalysts if they contain metallic components. When taking the activation process into consideration, the metal catalyst dissolved in the hydroxide solution preferably includes a metal oxide catalyst including oxygen.

In detail, the metal oxide catalyst includes one selected from the group consisting of $ZnO$, $Cu_2O$, $V_2O_5$, $Fe_2O_3$, $MnO_2$, $MgO$, $CrO_2$, $Al_2O_3$, and a mixture thereof.

The metal catalyst is ionized in the hydroxide solution through step (2). Preferably, 5 to 40 weight part of the metal catalyst is dissolved in 100 weight part of the hydroxide solution in step (2). If the ratio of the metal catalyst is less than the lower limit level, the amount of the metal catalyst is insufficient so that the sensitivity of the gas sensor may be degraded. If the ratio of the metal catalyst exceeds the upper limit level, the metal catalyst may not be sufficiently dissolved in the hydroxide solution, so that ion-size metal catalyst may not be introduced.

Various carbon materials generally known in the art can be used as the carbon material according to the present invention. In detail, the carbon material may include one selected from the group consisting of a single-wall carbon nano tube, a dual-wall carbon nano tube, a multi-wall carbon nano tube, a carbon fiber, a carbon black, a graphite, a char, a coal, a tar and a mixture thereof.

Preferably, the carbon material is immersed and stirred for 0.5 to 3 hours under the normal temperature in step (3). If the immersing and stirring time is less than the lower limit level, the hydroxide solution containing the ionized metal catalyst may not be sufficiently infiltrated into the carbon material. In addition, if the immersing and stirring time exceeds the upper limit level, there is no special benefit in practice.

Preferably, in step (3), 5 to 20 weight part of the carbon material is immersed and stirred in 100 weight part of the solution obtained through step (2). If the amount of the carbon material is less than the lower limit level, the conductive band of the carbon material may be damaged due to the strong activation reaction, so that the sensitivity of the gas sensor may be degraded. If the amount of the carbon material exceeds the upper limit level, the carbon material is not sufficiently activated, so that the sensitivity of the gas sensor may be degraded.

Preferably, in step (4), the heat-treating for the mixture is performed for 1 to 4 hours under the temperature range of 600° C. to 900° C. by rising the temperature at the rate of 5° C. to 10° C./min. If the temperature rising rate is less than the lower limit level, the reaction time may be lengthened, so that the energy consumption may be increased and undesired reaction may occur. In addition, if the temperature rising rate exceeds the upper limit level, the mixture is volatilized too much, so that the fine structure may not be easily formed in the carbon material. In addition, if the processing temperature and the processing time are less than the lower limit level, the thermal decomposition may not be perfectly achieved. In addition, if the processing temperature exceeds the upper limit level, the structural deformation may occur due to the high temperature. If the reaction time exceeds the upper limit level, there is no special benefit in practice and the undesired reaction may occur.

In step (5), the carbon material is repeatedly cleaned by using the distilled water until a cleaning liquid has a neutral PH after the cleaning. If the cleaning liquid does not represent the neutral PH, it signifies that the hydroxide solution remaining on the surface of the carbon material is insufficiently removed. In this case, it is impossible to retrieve only the carbon material containing the metal ion.

In step (6), the carbon material is preferably dried for 5 to 30 hours under the temperature range of 50° C. to 100° C. If the drying time and the drying temperature are less than the lower limit level, the carbon material may not be sufficiently dried. If the drying time and the drying temperature exceed the upper limit level, there is no special benefit in practice.

In step (7), the gas sensor can be manufactured by dispersing the carbon material obtained through step (6) in a dispersing solution and depositing the dispersing solution on the substrate formed thereon with an electrode.

The dispersing solution may include various solutions. For instance, the dispersing solution may include one selected from the group consisting of ethanol, methanol, acetone, dimethylformamid, and a mixture thereof. Preferably, the amount of the carbon material contained in the dispersing solution is 0.1 to 10 weight part based on 100 weight part of the dispersing solution. If the amount of the carbon material is less than 0.1 weight part, the carbon material may not be uniformly distributed on the substrate provided thereon with the electrode. If the amount of the carbon material exceeds 10 weight part, the carbon material may not be easily dispersed in the dispersing solution. The gas sensor can be manufactured as follows. The carbon material obtained through step (6) is uniformly dispersed in the dispersing solution according to the desired ratio. Then, the dispersing solution containing the carbon material is deposited on the substrate formed thereon with the wire electrode. The carbon material can be deposited through various schemes, such as vacuum deposition, spin coating, and spraying. FIG. 1 schematically shows the gas sensor manufactured through the above method.

In addition, the method according to the present invention may further include a step of heat-treating the gas sensor obtained through step (7). In this case, the heat-treating is performed for 0.1 to 3 hours under the temperature range of 30° C. to 100° C. If the heat-treating temperature and the heat-treating time are less than the lower limit level, the dispersing solution may not be easily evaporated. In addition, if the heat-treating time exceeds 3 hours, there is no special benefit in practice. Further, if the heat-treating temperature exceeds the upper limit level, a parafilm used for protecting a wire connection part may be melted.

The present invention also provides a high sensitive gas sensor using a carbon material containing an ionic metal catalyst manufactured through the above method.

Hereinafter, the present invention will be described in detail with reference to the embodiment and experimental example.

Embodiment

Manufacture of Gas Sensor Using Multi-Wall Carbon Nano Tube Containing Ionic Vanadium Oxide Catalyst A multi-wall carbon nano tube was selected as the carbon material.

First, 2M, 4M, 6M and 8M of the potassium hydroxide solutions were prepared by dissolving the potassium hydroxide in the distilled water.

Then, 3 g of vanadium oxide ($V_2O_5$) was added to 20 ml of each potassium hydroxide solution and the vanadium oxide was dissolved in each potassium hydroxide solution. When ionized, the vanadium oxide has a light green color, so the solution was sufficiently stirred until the solution represented the light green color.

Then, 1 g of the multi-wall carbon nano tube was immersed in the potassium hydroxide containing the vanadium oxide and stirred for 1 hour.

After rising the temperature to 750° C. by gradually increasing the temperature at the rate of 5° C./min, the heat treatment was performed for 1 hour under the above temperature. At this time, nitrogen gas was injected as inert gas at a rate of 20 cc/min.

After the heat treatment process has been completed, the multi-wall carbon nano tube was cleaned with distilled water by using an aspirator. The cleaning process was repeated until the cleaning liquid represented the neutral PH.

Then, the multi-wall carbon nano tube was dried in an oven for 10 hours under the temperature of 100° C.

After that, the multi-wall carbon nano tube was dispersed in the dimethylformamid. The ratio of the multi-wall carbon nano tube was 3 weight part based on 100 weight part of the dimethylformamid.

Then, the mixture solution obtained through the above procedure was dropped on the substrate formed thereon with the electrode, and the spin coating was performed for 4 minutes under the 900 RPM, thereby manufacturing the gas sensor.

Finally, the gas sensor deposited with the multi-wall carbon nano tube was heat-treated on a hot plate for 1 hour under the temperature of 50° C., thereby completing the manufacture of the gas sensor.

Comparative Example

The gas sensor was manufactured without adding or ionizing the vanadium oxide catalyst.

Surface Characteristic

Figure 3:
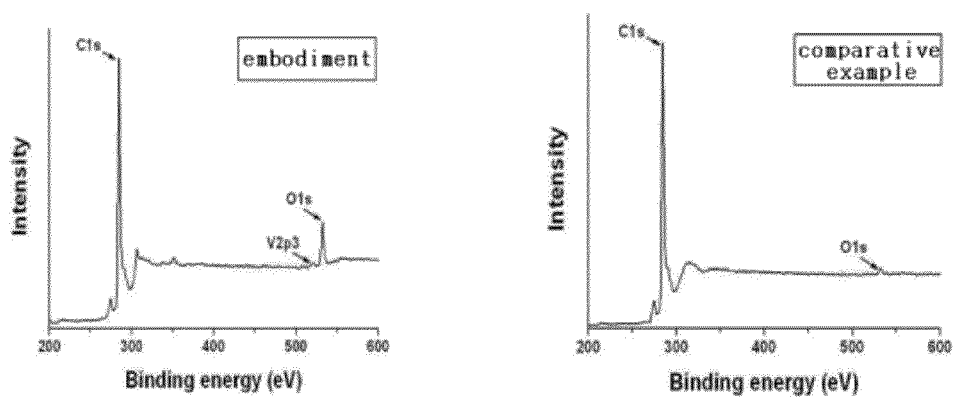
FIG. 3 is a graph showing the XPS analysis result for illustrating the surface composition of a gas sensor manufactured according to the embodiment of the present invention and the comparative example.

The XPS (X-ray photoelectron spectroscopy) analysis was carried out to estimate the surface characteristic of the gas sensor manufactured through the embodiment and the comparative example. FIG. 3 shows the estimation result. As can be seen from FIG. 3, the metal oxide ion was introduced onto the surface of the gas sensor manufactured according to the embodiment of the present invention.

Structural Characteristic

Figure 4:
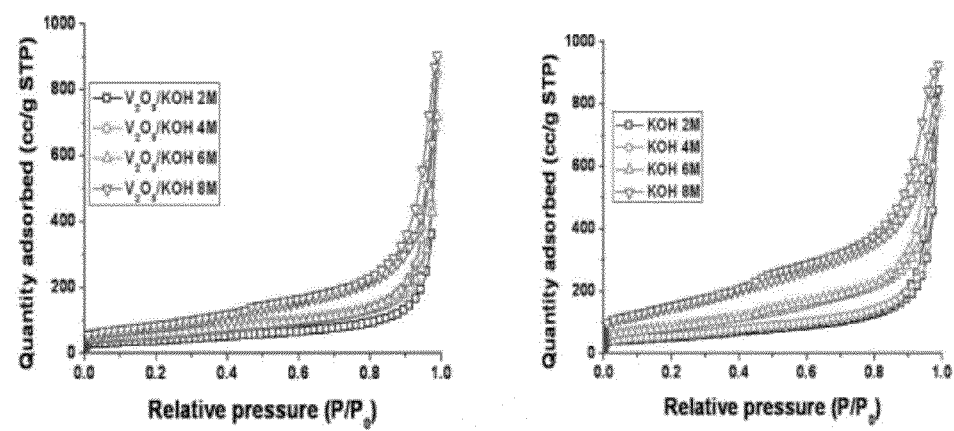
FIG. 4 is a graph showing the BET analysis result for illustrating the structural characteristics of a gas sensor manufactured according to the embodiment of the present invention and the comparative example.

The specific surface area characteristics were analyzed and shown in Table 1 and FIG. 4 in order to estimate the surface characteristic of the gas sensor manufactured through the embodiment and the comparative example.

TABLE 1

| Classification | | Specific surface area (cm$^3$/g) |
|---|---|---|
| Embodiment | $V_2O_5$/2M | 137 |
| | $V_2O_5$/4M | 193 |
| | $V_2O_5$/6M | 281 |
| | $V_2O_5$/8M | 492 |
| Comparative example | 2M | 181 |
| | 4M | 203 |
| | 6M | 301 |
| | 8M | 549 |

As can be seen from Table 1 and FIG. 4, the specific surface area was increased as the mole number of the potassium hydroxide solution increases. When the vanadium oxide ($V_2O_5$) was ionized, the mass of the multi-wall carbon nano tube was increased due to the introduction of the vanadium oxide, so that the specific surface area of the embodiment was smaller than the specific surface area of the comparative example.

Gas Sensitivity Characteristic Evaluation

Figure 5:
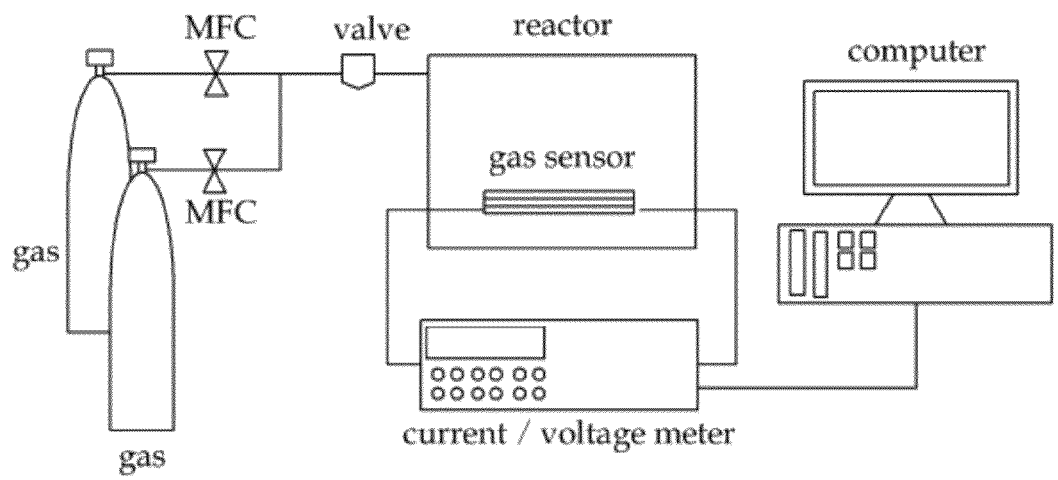
FIG. 5 is a schematic view showing an apparatus for measuring gas sensitive characteristics of a gas sensor.
Figure 6:
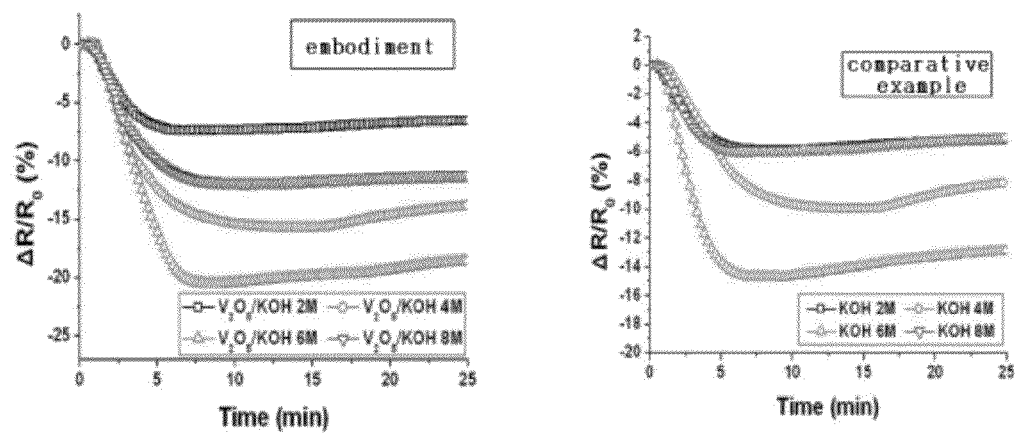
FIG. 6 is a graph showing gas sensitive characteristics of a gas sensor manufactured according to the embodiment of the present invention and the comparative example.

The gas sensitivity characteristics of the gas sensor manufactured through the embodiment and the comparative example were estimated. The gas sensitivity characteristics were estimated by using the apparatus as shown in FIG. 5 while injecting NO gas in the density of 50 ppm under the temperature of 25° C. The estimation result is shown in Table 2 and FIG. 6. In FIG. 6, the X-axis represents measurement time and the Y-axis represents the resistance variation.

TABLE 2

| Classification | | Resistance variation (%) | Reaction time | Reaction rate (%/min) |
|---|---|---|---|---|
| Embodiment | $V_2O_5$/KOH 2M | −7.4 | 6 | −1.2 |
| | $V_2O_5$/KOH 4M | −15.5 | 13 | −1.2 |
| | $V_2O_5$/KOH 6M | −20.5 | 7.5 | −2.7 |
| | $V_2O_5$/KOH 8M | −12 | 7 | −1.7 |
| Comparative example | KOH 2M | −5 | 6 | −0.8 |
| | KOH 4M | −10 | 12 | −0.8 |
| | KOH 6M | −15 | 6 | −2.5 |
| | KOH 8M | −6 | 5.5 | −1.1 |

The resistance variation represents the sensitivity of the gas sensor and the sensitivity of the gas sensor is increased as the absolute value of the resistance variation is increased. As can be seen from Table 2, the gas sensor manufactured according to the embodiment of the present invention represents the absolute value of the resistance variation higher than that of the gas sensor manufactured according to the comparative example.

In addition, the reaction rate signifies the response rate of the gas sensor, and the response rate becomes high as the absolute value of the reaction rate is increased. As can be seen from Table 2, the gas sensor manufactured according to the embodiment of the present invention represents the absolute value of the reaction rate higher than that of the gas sensor manufactured according to the comparative example.

That is, according to the embodiment of the present invention, the gas sensor having high sensitivity even in the normal temperature can be obtained.

Although the exemplary embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A method of manufacturing a high sensitive gas sensor using a carbon material containing an ionized metal catalyst, the method comprising the steps of:
   (1) preparing a hydroxide solution by dissolving a hydroxide in a distilled water;
   (2) dissolving a metal catalyst in the hydroxide solution;
   (3) immersing the carbon material in a solution obtained through step (2) and stirring the carbon material;
   (4) heat-treating a mixture obtained through step (3);
   (5) cleaning the heat-treated carbon material obtained through step (4);
   (6) drying the carbon material cleaned through step (5); and
   (7) manufacturing the gas sensor by loading the carbon material obtained through step (6) on a substrate.

2. The method of claim 1, wherein the hydroxide includes one selected from the group consisting of a potassium hydroxide, a sodium hydroxide, a lithium hydroxide, a rubidium hydroxide, a cesium hydroxide and a mixture thereof.

3. The method of claim 1, wherein a density of the hydroxide solution prepared through step (1) is in a range of 2M to 8 M.

4. The method of claim 3, wherein the density of the hydroxide solution prepared through step (1) is in a range of 4M to 6M.

5. The method of claim 1, wherein the metal catalyst dissolved in the hydroxide solution in step (2) includes a metal oxide catalyst including oxygen.

6. The method of claim 5, wherein the metal oxide catalyst includes one selected from the group consisting of ZnO, $Cu_2O$, $V_2O_5$, $Fe_2O_3$, $MnO_2$, MgO, $CrO_2$, $Al_2O_3$, and a mixture thereof.

7. The method of claim 1, wherein 5 to 40 weight part of the metal catalyst is dissolved in 100 weight part of the hydroxide solution in step (2).

8. The method of claim 1, wherein the carbon material used in step (3) includes one selected from the group consisting of a single-wall carbon nano tube, a dual-wall carbon nano tube, a multi-wall carbon nano tube, a carbon fiber, a carbon black, a graphite, a char, a coal, a tar and a mixture thereof.

9. The method of claim 1, wherein the carbon material is immersed and stirred for 0.5 to 3 hours under a normal temperature in step (3).

10. The method of claim 1, wherein, in step (3), 5 to 20 weight part of the carbon material is immersed and stirred in 100 weight part of the solution obtained through step (2).

11. The method of claim 1, wherein, in step (4), the heat-treating for the mixture is performed for 1 to 4 hours under a temperature range of 600° C. to 900° C. by rising a temperature at a rate of 5° C. to 10° C./min.

12. The method of claim 1, wherein, in step (5), the carbon material is repeatedly cleaned by using the distilled water until a cleaning liquid has a neutral PH after the cleaning.

13. The method of claim 1, wherein, in step (6), the carbon material is dried for 5 to 30 hours under a temperature range of 50° C. to 100° C.

14. The method of claim 1, wherein, in step (7), the gas sensor is manufactured by dispersing the carbon material obtained through step (6) in a dispersing solution and depositing the dispersing solution on the substrate formed thereon with an electrode.

15. The method of claim 14, wherein the dispersing solution includes one selected from the group consisting of ethanol, methanol, acetone, dimethylformamid, and a mixture thereof.

16. The method of claim 14, wherein an amount of the carbon material contained in the dispersing solution is 0.1 to 10 weight part based on 100 weight part of the dispersing solution.

17. The method of claim 14, further comprising a step of heat-treating the gas sensor obtained through step (7).

18. The method of claim 17, wherein the heat-treating is performed for 0.1 to 3 hours under a temperature range of 30° C. to 100° C.

* * * * *